United States Patent
Onishi et al.

(10) Patent No.: US 6,214,435 B1
(45) Date of Patent: Apr. 10, 2001

(54) AMINIUM COMPOUNDS AND OPTICAL INFORMATION RECORDING MEDIA CONTAINING THE SAME

(75) Inventors: Masao Onishi, Saitama; Tadayuki Kiyoyanagi, Tokyo, both of (JP)

(73) Assignee: Nippon Kayaku Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/423,263

(22) PCT Filed: May 13, 1998

(86) PCT No.: PCT/JP98/02113

§ 371 Date: Dec. 20, 1999

§ 102(e) Date: Dec. 20, 1999

(87) PCT Pub. No.: WO98/51661

PCT Pub. Date: Nov. 19, 1998

(30) Foreign Application Priority Data

May 14, 1997 (JP) .................................................. 9-138010

(51) Int. Cl.⁷ ...................................................... B32B 3/02
(52) U.S. Cl. .................................... 428/64.4; 430/270.19; 558/46; 558/58; 558/53; 562/83; 562/84; 562/59; 562/46; 562/47
(58) Field of Search ................................ 558/46, 58, 53; 562/83, 84, 59, 46, 47; 430/270.19; 428/64.4

(56) References Cited

U.S. PATENT DOCUMENTS 5,605,732  2/1997  Mihara et al. .................. 428/64.8

FOREIGN PATENT DOCUMENTS

| | | |
|---|---|---|
| 0 554 627 | 8/1993 | (EP) . |
| 43-25335 | 11/1968 | (JP) . |
| 58-99447 | 6/1983 | (JP) . |
| 60-219289 | 11/1985 | (JP) . |
| 60-236131 | 11/1985 | (JP) . |
| 61-22984 | 1/1986 | (JP) . |
| 61-69991 | 4/1986 | (JP) . |
| 63-51462 | 3/1988 | (JP) . |
| 64-38490 | 1/1989 | (JP) . |
| 64-75454 | 3/1989 | (JP) . |
| 1-99885 | 4/1989 | (JP) . |
| 2-311447 | 12/1990 | (JP) . |
| 3-16785 | 1/1991 | (JP) . |
| 4-349462 | 1/1991 | (JP) . |
| 4-202681 | 7/1992 | (JP) . |
| 4-240603 | 8/1992 | (JP) . |
| 5-247437 | 9/1993 | (JP) . |
| 6-220420 | 8/1994 | (JP) . |
| 7-196588 | 8/1995 | (JP) . |
| 9-150573 | 6/1997 | (JP) . |

*Primary Examiner*—Samuel Barts
(74) *Attorney, Agent, or Firm*—Nields & Lemack

(57) ABSTRACT

A novel aminium compound exhibiting excellent solubility for solvents and high safety in terms of handling and environment is provided.

An aminium compound represented by the following formula (1):

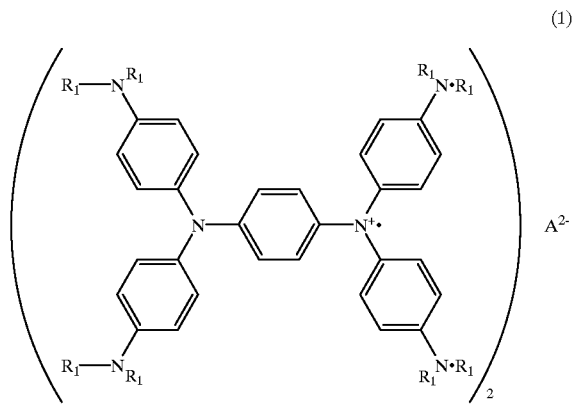

wherein $R_1$ represents substituted or unsubstituted alkyl and $A^{2-}$ represents a divalent organic anion.

11 Claims, No Drawings

AMINIUM COMPOUNDS AND OPTICAL INFORMATION RECORDING MEDIA CONTAINING THE SAME

This application is a 371 of PCT/JP98/02113 filed May 13, 1998.

FIELD OF THE INVENTION

The present invention relates to aminium compounds and optical information recording media containing the same. More specifically, it relates to aminium compounds having divalent organic anions as counterions as well as optical information recording media containing the aminium compounds and, for example, cyanine dyes, having improved light fastness and useful for recording and reproduction of information or the formation of images by irradiating laser light.

PRIOR ARTS

Various dyes including phthalocyanine derivatives and cyanine dyes of indolenine type have been proposed as organic dyes useful for recording media, especially write-once CD-R and DVD-R. Phthalocyanine dyes are excellent in light fastness and storage stability, but almost insoluble in the solvents which do not etch conventionally used materials such as polycarbonate. Thus, a solution to be applied onto a substrate having the desired concentration of the dye cannot be obtained. On the other hand, cyanine dyes are soluble in solvents to some extent, but few solvents are suitable for practical use. Further, cyanine dyes have poor light fastness and storage stability and thus, in order to prevent the deterioration of cyanine dyes by light, a singlet oxygen quencher is usually added. The addition of organometallic complexes such as nickel complexes and salts of aminium or diimonium as described in JP-94026028B and JP-1099885A as the singlet oxygen quencher is known to improve light fastness of cyanine dyes and polymethine dyes which are easily deteriorated by oxygen due to their autosensitization. However, the nickel complexes have generally poor solubilities into organic solvents. And, the presence of a metal causes problems in terms of handling or environment. Although the salts of aminium and diimonium with various counterions such as perchlorate and antimony hexafluoride are known, perchlorate salts cause problem in terms of handling since they are hazardous chemicals. Antimony hexafluoride salts have a poor solubility for solvents, especially when combined with methine dyes and thus their coating solutions can be hardly recycled. The presence of metal causes environmental pollution.

An object of the present invention is to provide a novel aminium compound excellent in solubility for solvents and safe in terms of handling and environment as well as an optical information recording medium comprising the same.

SUMMARY OF THE INVENTION

The present inventors have made earnest researches into solution of the above-mentioned problem. As a result, they have found that an aminium compound of the following formula (1) has a good solubility for solvents, especially when combined with a methine dye, that an optical information recording material having excellent stability and light fastness can be obtained by including at least one of the aminium compounds into an optical information recording medium, and that the solution of the aminium compound can be recycled.

That is, the present invention relates to:
(1) an aminium compound of the following formula (1):

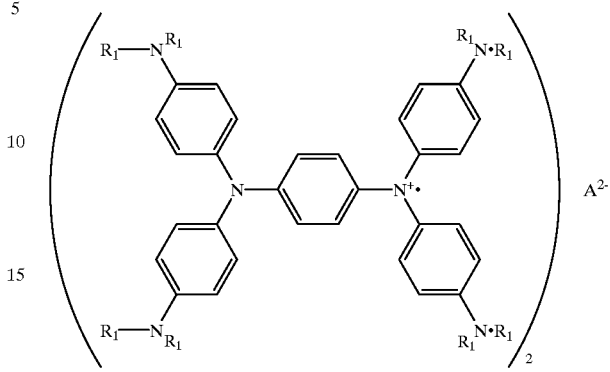

(1)

wherein $R_1$ represents substituted or unsubstituted alkyl and $A^{2-}$ represents a divalent organic anion;
(2) an aminium compound as defined in (1) wherein $R_1$ is $C_2$–$C_4$ alkyl;
(3) an aminium compound as defined in (1) wherein $R_1$ is n-butyl;
(4) an aminium compound as defined in any one of (1) to (3) wherein $A^{2-}$ is an ion of an aromatic disulfonic acid having two sulfonic acid groups within its molecule;
(5) an aminium compound as defined in (4) wherein the organic anion is a naphthalenedisulfonic acid ion;
(6) an aminium compound as defined in (5) wherein the naphthalenedisulfonic acid ion is an ion of a compound represented by the following formula (2)

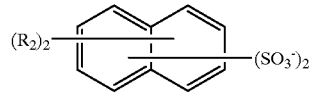

(2)

wherein $R_2$ represents independently hydrogen, halogen, lower alkyl, hydroxyl, alkylamino, amino, acetyl, —$NHCOR_3$, —$NHSO_2R_3$ or —$OSO_2R_3$ in which $R_3$ is substituted or unsubstituted aryl or substituted or unsubstituted alkyl;
(7) an aminium compound as defined in (6) wherein $R_2$ is independently hydrogen, hydroxyl, —$NHCOR_3$, —$NHSO_2R_3$ or —$OSO_2R_3$;
(8) an aminium compound as defined in (6) wherein $R_2$ is hydrogen or hydroxyl;
(9) an optical information recording medium comprising at least one aminium compound as defined in any one of (1) to (8) in a recording layer;
(10) an optical information recording medium as defined in (9) which further comprises a methine compound in the recording layer;
(11) an optical information recording medium as defined in (10) wherein the methine compound is a cyanine dye; and
(12) an optical information recording medium as defined in (11) wherein the aminium compound is used in an amount of 10 to 150 parts by weight per 100 parts by weight of the cyanine dye.

Best Mode for Carrying Out the Invention

An unsubstituted alkyl group represented by $R_1$ in the general formula (1) is specifically a C1–C12 alkyl group such as methyl, ethyl, propyl, isopropyl, 2-methylpropyl, n-butyl, t-butyl, pentyl, hexyl or dodecyl, preferably C2–C4 alkyl, more preferably n-butyl. Substituents in substituted alkyl groups include halogen, alkyloxy, alkyloxyalkyloxy, aryl and hydroxyl. Specifically, the substituted alkyl group is a C1–C9 substituted alkyl group such as hydroxymethyl, methoxyethyl, ethoxyethyl, butoxyethyl, phenylethyl, phenylpropyl, benzyl, tetrafluoropropyl, trifluoroethyl, methoxyethyloxyethyl, methoxypropyl, hydroxypropyl, furfuryl or acetyloxyethyl, preferably C2–C6 substituted alkyl.

A divalent organic anion represented by $A^{2-}$ is preferably an ion of an aromatic disulfonic acid having two sulfonic acid groups within its molecule, example of which includes an ion of naphthalenedisulfonic acid derivatives such as naphthalene-1,5-disulfonic acid, R acid, G acid, H acid, benzoyl H acid (a benzoyl group being attached to an amino group of H acid), p-chlorobenzoyl H acid, p-toluenesulfonyl H acid, chloro H acid (an amino group of H acid being replaced with a chlorine atom), chloroacetyl H acid, metanyl γ acid, 6-sulfonaphthyl-γ acid, C acid, ε acid, p-toluenesulfonyl R acid, naphthalene-1,6-disulfonic acid or 1-naphthol-4,8-disulfonic acid; carbonyl J acid, 4,4'-diaminostilbene-2,2'-disulfonic acid, di-J acid, naphthalic acid, naphthalene-2,3-dicarboxylic acid, diphenic acid, stilbene-4,4'-dicarboxylic acid, 6-sulfo-2-oxy-3-naphthoic acid, anthraquinone-1,8-disulfonic acid, 1,6-diaminoanthraquinone-2,7-disulfonic acid, 2-(4-sulfophenyl)-6-aminobenzotriazole-5-sulfonic acid, 6-(3-methyl-5-pyrazolonyl)-naphthalene-1,3-disulfonic acid, 1-naphthol-6-(4-amino-3-sulfo)anilino-3-sulfonic acid or the like. More preferable divalent organic anion is an ion of naphthalenedisulfonic acid. Even more preferable divalent organic anion is an ion of a compound represented by the aforementioned formula (2).

In the aforementioned formula (2), $R_2$ is independently hydrogen, halogen, lower alkyl, hydroxyl, alkylamino, amino, acetyl, —$NHCOR_3$, —$NHSO_2R_3$ or —$OSO_2R_3$ in which $R_3$ is substituted or unsubstituted aryl or substituted or unsubstituted alkyl. The halogen atoms include fluorine, chlorine, bromine and iodine. Examples of the lower alkyl groups include C1–C4 alkyl as illustrated with respect to the unsubstituted alkyl group represented by $R_1$. Example of the alkylamino group includes C1–C4 alkylamino. Examples of the substituted or unsubstituted aryl groups represented by $R_3$ include phenyl, toluyl, 4-chlorophenyl, naphthyl, nitrophenyl and butylphenyl. Examples of the substituted or unsubstituted alkyl groups include a C1–C8 alkyl group such as methyl, ethyl, propyl, butyl, pentyl, octyl, chloromethyl, chloroethyl, methoxyethyl, isobutyl, methoxyethyl or butoxyethyl. Preferably, the ion of the compound represented by the formula (2) is an ion of naphthalenedisulfonic acid having no substituent other than the sulfonyl groups or a hydroxyl group in addition to the sulfonyl groups such as naphthalene-1,5-disulfonic acid, naphthalene-1,6-disulfonic acid, or 1-naphthol-4,8-disulfonic acid.

Non-limiting examples of the compound of formula (1) of the present invention are illustrated in the following table. In this table, Bu, Et, Pr, Bz and Ph represent n-butyl, ethyl, n-propyl, benzyl and phenyl, respectively.

TABLE 1

| | $R_1$ | $A^{2-}$ |
|---|---|---|
| 1 | Bu | naphthalene-1,5-disulfonic acid ion |
| 2 | Bu | naphthalene-2,6-disulfonic acid ion |
| 3 | Bu | 2-naphthol-3,6-disulfonic acid ion |
| 4 | Bu | H acid (deprotonated form) |

TABLE 1-continued

| | $R_1$ | $A^{2-}$ |
|---|---|---|
| 5 | Bu | carbonyl J acid (deprotonated form) |
| 6 | Bu | 2-naphthol-6,8-disulfonic acid ion |
| 7 | Bu | Aniline-2,5-disulfonic acid ion |
| 8 | Bu | 1-(1,3-disulfonato-6-naphthyl)-3-methyl-5-pyrazolone (deprotonated form) |
| 9 | Bu | 6-amino-2-(4-sulfonatophenyl)-5-sulfonatobenzotriazole (deprotonated form) |
| 10 | Bu | p-chlorobenzoyl H acid (deprotonated form) |
| 11 | Bu | Benzoyl H acid (deprotonated form) |
| 12 | Bu | 2-hydroxy-3-(3-methyl-5-pyrazolon-1-yl)-5-sulfonatobenzoate (deprotonated form) |
| 13 | Bu | p-toluenesulfonyl H acid (deprotonated form) |
| 14 | Bu | chloro H acid (deprotonated form) |
| 15 | Bu | chloroacetyl H acid (deprotonated form) |
| 16 | Bu | DJ acid (deprotonated form) |
| 17 | Bu | 4-amino-3-sulfonatophenyl J acid (deprotonated form) |
| 18 | Bu | 3-sulfonatophenyl J acid (deprotonated form) |
| 19 | Bu | 6-sulonatonaphthyl J acid (deprotonated form) |
| 20 | Bu | 1-naphthol-3,8-disulfonic acid ion |
| 21 | Bu | 2,7-disulfonatonaphthyl-3-p-toluensulfonic acid ion |
| 22 | Bu | naphthalene-1,6-disulfonic acid ion |
| 23 | Bu | 1-naphthol-4,8-disulfonic acid ion |
| 24 | Bu | 1-amino-8-hydroxy-2,4-disulfonato-naphthalene (deprotonated form) |
| 25 | Et | naphthalene-1,5-disulfonic acid ion |
| 26 | Pr | naphthalene-2,6-disulfonic acid ion |
| 27 | Bz | 2-naphthol-3,6-disulfonic acid ion |
| 28 | $CH_3CF_2CF_2$— | 2-naphthol-6,8-disulfonic acid ion |
| 29 | $CH_3OCH_2CH_2$— | naphthalene-1,5-disulfonic acid ion |
| 30 | $BzOCH_2CH_2$— | 1-naphthol-3,8-disulfonic acid ion |
| 31 | Ph—$(CH_2)_3$— | 1-naphthol-4,8-disulfonic acid ion |
| 32 | $H(CF_2)_8CH_2$— | naphthalene-1,6-disulfonic acid ion |
| 33 | $H(CF_2)_2CH_2$— | naphthalene-2,6-disulfonic acid ion |

The compound of general formula (1) can be synthesized by oxidizing 1 mole of the corresponding phenylenediamine derivative with approximately 1 mole of an oxidizing agent such as silver nitrate, silver perchlorate or cupric chloride in an organic solvent, preferably a water-soluble polar solvent such as DMF, DMI or NMP, generally at 0 to 100° C., preferably 5 to 70° C. To the reaction mixture is added a solution of an acid of the corresponding divalent organic anion or its salt in a solvent, preferably a water-soluble polar solvent such as DMF, DMI, or NMP, or aqueous solvent thereof. The reaction mixture is then diluted with water. Alternatively, the dye once separated in the form of the salt such as a nitrate salt or a perchlorate salt is re-dissolved in a water-soluble solvent such as alcohol, DMF or acetic acid, or aqueous solvent thereof, together with an acid or salt of a desired divalent organic anion to effect salt-exchange. In this connection, the phenylenediamine derivative is known as described in, for example, U.S. Pat. Nos. 3,771,793 and 3,715,386 and JP-84040825B.

The recording medium of the present invention comprises a substrate and a recording layer applied thereon, the recording layer containing the aminium compound represented by the aforementioned formula (1) and optionally any dye such as a methine compound e.g. a cyanine dye. The recording medium has a reflective layer and optionally a surface coat layer. It is useful as write-once CD-R, DVD-R and the like. The aminium compound of the present invention can be used in an amount of 10 to 150 parts by weight, preferably 10 to 100 parts by weight, per 100 parts by weight of a methine compound, or generally in an amount of 0.01 to 10 moles, preferably 0.1 to 2 moles, more preferably 0.2 to 1 mole, per 1 mole of a methine compound.

Examples of methine compounds include cyanine dyes, polymethine dyes, squalilium dyes and azurene dyes, the cyanine dyes being preferable. The cyanine dyes include dyes of indolenine, quinoline, oxazole and thiazole types. A methine compound may be used alone or in combination with other methine compound(s). It may be used in combination with any other dye(s) such as indoaniline dyes, phthalocyanine dyes, azo dyes and the like.

An aminium compound may be used alone or in combination with other aminium compound(s) in the optical information recording medium of the present invention. Various additives including an oxidizing agent, a UV absorber and a singlet oxygen quencher may be combined in order to improve reading durability and light fastness. The singlet oxygen quenchers include common transition metal complexes such as nickel complexes and nitroso compounds. Various resins may be combined as well.

As a substrate, any known substance such as glass, metallic plates or plastics can be used in the present invention. The plastics include acrylic, polycarbonate, methacrylic, polysulfone, polyimide, amorphous polyolefine, polyester and polypropylene resins. The substrate may be formed into various shapes such as a disc, a card, a sheet and a roll film.

A guide groove may be formed on a glass or plastic substrate in order to make the tracking on recording easy. And, an undercoat layer comprising a plastic binder, an inorganic oxide or sulfide or the like may be provided on a glass or plastic substrate. Preferably, the undercoat layer has a thermal conductivity lower than that of a substrate.

The recording layer of the present invention can be prepared by dissolving the aminium compound and optionally a dye such as a methine compound in an organic solvent such as tetrafluoropropanol, diacetone alcohol, methanol, ethanol, butanol, methyl cellosolve, ethyl cellosolve, isopropyl alcohol, acetone, methylethylketone, dichloroethane, dichloromethane, propylene glycol monomethylether monoacetate, cyclohexanone, 3-hydroxy-3-methyl-2-butanone and the like, if necessary adding a suitable binder, and applying the resultant solution onto a substrate using a spin coater, a roll coater, a bar coater or the like. Alternatively, it can be prepared by means of vacuum deposition, spattering, doctor blade process, casting or dipping wherein a substrate is dipped in the above solution.

Thickness of the recording layer is 0.01 to 5 $\mu$m, preferably 0.02 to 3 $\mu$m. When the reading is effected by reflection, the thickness of the recording layer is more preferably odd quarters of the wavelength of a laser used for reading.

If necessary, the optical information recording medium of the present invention may have an undercoat layer on a substrate, a protective layer on a recording layer or a reflective layer either on a substrate or on a recording layer. A reflective layer is provided by means of vacuum deposition, spattering or ion plating, or using the silver mirror reaction, that is, the reduction of a salt or complex of a metal such as gold, silver or copper.

In the optical information recording medium of the present invention, the recording of informations or the formation of images is effected by irradiating a recording layer with a spot-focused high energy beam of semiconductor laser, helium-neon laser, He-Cd laser, YAG laser, Ar laser or the like through a substrate or from the other side than the substrate side. The reading of information or images is effected by irradiating with a low output laser beam so that the difference in an amount of a reflected or transmitted light between pitted parts and unpitted parts is detected.

EXAMPLES

The present invention will be described in more detail by way of the following examples which are not intended to limit the scope of the claimed invention. All parts referred to herein are by weight unless otherwise indicated.

Example 1

2.3 Parts of N,N,N',N'-tetrakis(p-dibutylaminophenyl)-p-phenylenediamine was added to 12.5 parts of DMF and dissolved by heating at 60° C. Then, 0.43 part of silver nitrate in 12.5 parts of DMF was added thereto and reacted for 30 minutes. After cooling, silver was precipitated which was filtered off. To this reaction mixture was added dropwise 0.62 part of disodium naphthalene-1,5-disulfonic acid in 7 parts of 43% aqueous DMF and the reaction mixture was then stirred for 5 minutes. 25 parts of 48% aqueous DMF was then added dropwise slowly with the subsequent stirring for 10 minutes. Further, 12.5 parts of water was added dropwise and then the reaction mixture was stirred for 15 minutes. The green crystals were obtained by filtration and then washed with 150 parts of water to provide a cake. The cake was dried to obtain 2.7 parts of the present compound No. 1 as green crystals. $\lambda$max: 950, 1480 nm (acetone)

TABLE 2

| | Elementary analysis | |
|---|---|---|
| | calculated (%) | found (%) |
| C | 75.59 | 75.10 |
| H | 8.99 | 9.22 |
| N | 7.89 | 8.30 |

Other compounds can be synthesized in the same manner as described above, by oxidizing the corresponding phenylenediamine derivatives with an oxidizing agent and then reacting the resulting compound with the corresponding divalent organic anions.

Solubilities of the present compound No. (1) in diacetone alcohol (DAA) and in tetrafluoropropanol (TFP) at room temperature were 34% by weight or more and 12% by weight or more, respectively, while the known compound A, i.e. the compound of the formula (1) wherein $R_1$ is n-butyl and A is an antimony hexafluoride ion has the solubility of 18% by weight in DAA and 9% by weight in TFP at the same temperature. Thus, the solubilities of the present compound were higher. In case of the present compound No. 1, no insoluble substance was observed after adding it in an amount of 0.6% by weight to a solution containing 1% by weight of pentamethine cyanine dye in TFP, while, in case of the known compound A, insoluble substance was observed after adding it in an amount of 0.6% by weight in the same solution. As evident from the above, the solubility of the present compound No. (1) was higher even in the presence of a cyanine dye.

Example 2: light fastness test

A coating solution was prepared by adding 10, 20 or 60% by weight of the present compound No. (1) obtained in Example 1 or the known compound A used in Example 1 as a comparative compound into a solution of 0.10 part of pentamethine cyanine dye in 10 parts of TFP. The thus-prepared coating solution was applied onto a polycarbonate substrate by spin coating at 2000 rpm to obtain a dye film. The dye film together with the Blue Scale was put into the UV long life carbon arc apparatus for testing light fastness (ex. Suga Shiken-ki; black panel temperature=63° C.) and irradiated with a light through the substrate for 6, 20 or 50 hours to conduct a light fastness test. Light fastness of the dye film was determined by visual observation of the fading of the film according to the Blue Scale.

TABLE 3

| | Amount added/ cyanine dye | Rank of light fastness |
|---|---|---|
| present compound No. 1 | 10 wt % | 1–2 |
| | 20 wt % | 3 |
| | 60 wt % | 5 |
| comparative compound A | 10 wt % | 1–2 |
| | 20 wt % | 3 |
| | 60 wt % | not determined* |

*Insoluble substance was observed in the coating solution.

As shown in the above results, the light fastness is improved with the increase in an amount of each compound. The addition of 60% by weight of the comparative compound A with respect to the amount of a cyanine dye (corresponding to 0.6% by weight with respect to the amount of TFP; the result of Example 1 shows that the comparative compound A is soluble in TFP at the concentration of 9% by weight with respect to the amount of TFP, while addition of 0.6% by weight of the comparative compound A in combination with a cyanine dye produced insoluble substance) produced insoluble substance and thus did not result in higher light fastness of the dye film.

Example 3

A coating solution was prepared by dissolving 0.06 part of the present compound No. (1) obtained in Example 1 and 0.10 part of pentamethine cyanine dye in 10 parts of tetrafluoropropanol and by passing through a 0.2 μm filter. 5 ml of the thus-prepared solution was pipetted onto a grooved polycarbonate resin substrate (5 in.) and coated using a spin coater. The substrate was dried at 50° C. for 5 minutes to prepare a recording layer. Maximum wavelength of absorption of the coated film was 719 nm. The coated film was irradiated with a semiconductor laser beam having a central wavelength of 780 nm to form pits having clear profiles. Storage stability of the coated film was 10 days or more under the condition of 60° C. and 80% RH.

Effect of the Invention

The aminium compound of the present invention has high solubility for organic solvents, especially when combined with dyes so that a coating solution having higher concentration can be prepared and a dye film can be easily obtained by applying the coating solution. In addition, due to high solubility, the coating solution excellent in storage stability and recyclable can be obtained. The use of the aminium compound provides an optical information recording medium having high light fastness.

What is claimed is:

1. An aminium compound represented by the following formula (1):

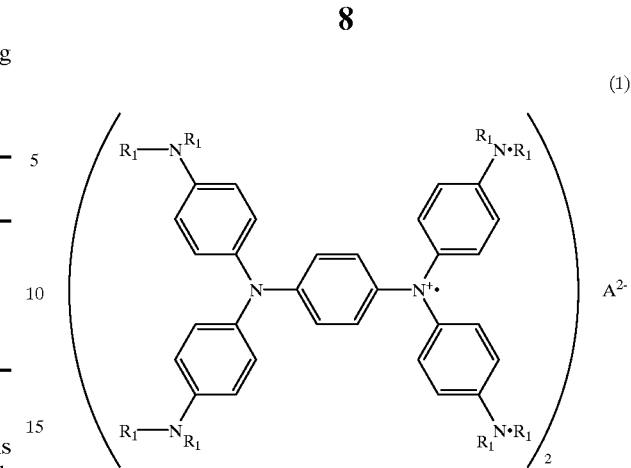

wherein $R_1$ represents substituted or unsubstituted alkyl and $A^{2-}$ represents a divalent organic anion having two sulfonic acid groups within its molecule.

2. An aminium compound as claimed in claim 1 wherein $R_1$ is $C_2$–$C_4$ alkyl.

3. An aminium compound as claimed in claim 1 wherein $R_1$ is n-butyl.

4. An aminium compound as claimed in any one of claims 1 to 3 wherein the organic anion is a naphthalenedisulfonic acid ion.

5. An aminium compound as claimed in claim 4 wherein the naphthalenedisulfonic acid ion is an ion of a compound represented by the following formula (2):

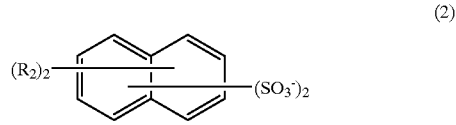

wherein $R_2$ represents independently hydrogen, halogen, lower alkyl, hydroxyl, alkylamino, amino, acetyl, —$NHCOR_3$, —$NHSO_2R_3$ or —$OSO_2R_3$ in which $R_3$ is substituted or unsubstituted aryl or substituted or unsubstituted alkyl.

6. An aminium compound as claimed in claim 5 wherein $R_2$ is independently hydrogen, hydroxyl, —$NHCOR_3$, —$NHSO_2R_3$ or —$OSO_2R_3$.

7. An aminium compound as claimed in claim 5 wherein $R_2$ is hydrogen or hydroxyl.

8. An optical information recording medium comprising at least one aminium compound as claimed in claim 1 in a recording layer.

9. An optical information recording medium as claimed in claim 8 which further comprises a methine compound in the reording layer.

10. An optical information recording medium as claimed in claim 9 wherein the methine compound is a cyanine dye.

11. An optical information recording medium as claimed in claim 10 wherein the aminium compound is used in an amount of 10 to 150 parts by weight per 100 parts by weight of the cyanine dye.

* * * * *